(12) United States Patent
Fuertes

(10) Patent No.: US 10,440,974 B2
(45) Date of Patent: Oct. 15, 2019

(54) METHIONINE-RICH COMPOSITION FOR FEEDING ANIMALS

(71) Applicant: Evonik Degussa GmbH, Essen (DE)

(72) Inventor: Patrick Fuertes, Lomme (FR)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/399,764

(22) Filed: Jan. 6, 2017

(65) Prior Publication Data

US 2017/0112166 A1  Apr. 27, 2017

Related U.S. Application Data

(63) Continuation of application No. 13/501,490, filed as application No. PCT/EP2010/065428 on Oct. 14, 2010, now abandoned.

(30) Foreign Application Priority Data

Oct. 14, 2009 (FR) ...................... 09 57183

(51) Int. Cl.
| | |
|---|---|
| *A23K 20/142* | (2016.01) |
| *C12P 13/12* | (2006.01) |
| *A23L 5/20* | (2016.01) |
| *C12P 13/06* | (2006.01) |

(52) U.S. Cl.
CPC .............. *A23K 20/142* (2016.05); *A23L 5/20* (2016.08); *C12P 13/06* (2013.01); *C12P 13/12* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2,098,923 A | 11/1937 | Mertz | |
| 2,446,913 A | 8/1948 | Erlich | |
| 2,470,500 A | 5/1949 | Lawrence | |
| 2,713,592 A | 7/1955 | Hoglan | |
| 3,139,386 A | 6/1964 | Takesue et al. | |
| 4,148,688 A | 4/1979 | Yamada et al. | |
| 5,622,710 A | 4/1997 | Binder et al. | |
| 6,417,395 B1 | 7/2002 | Ponceblanc et al. | |
| 7,195,897 B2 | 3/2007 | Leonbartsberger et al. | |
| 2004/0033573 A1 | 2/2004 | Norddahl et al. | |
| 2005/0089975 A1 | 4/2005 | Lorbert et al. | |
| 2007/0122888 A1 | 5/2007 | Boy et al. | |

FOREIGN PATENT DOCUMENTS

| | | |
|---|---|---|
| AU | 664642 | 11/1995 |
| CA | 2 285 820 | 4/2000 |
| CA | 2285820 | 4/2000 |
| EP | 0588707 | 3/1994 |
| EP | 0 992 490 | 4/2000 |
| EP | 2 133 328 | 12/2009 |
| GB | 1296347 | 11/1972 |
| WO | 2004/038013 | 5/2004 |
| WO | WO 2005/007862 | 1/2005 |
| WO | 2005/111202 | 11/2005 |
| WO | 2006/001616 | 1/2006 |
| WO | 2006/138689 | 12/2006 |
| WO | 2007/012078 | 1/2007 |
| WO | 2007/017710 | 2/2007 |
| WO | 2007/077041 | 7/2007 |
| WO | WO 2007/135188 | 11/2007 |
| WO | WO 2009/043803 | 4/2009 |

OTHER PUBLICATIONS

Written Opinion in International Application No. PCT/EP2010/065428, dated Feb. 17, 2011, pp. 1-5.
Toyokichi, et al. "Ultrafiltration Process, Derwent Abstract" JP 59014795, Jan. 25, 1984, p. 1.
Leuchtenberger, et al. "Feed Additive for Animals Based on Aminoacid from Fermentative Liquor, Process for Its Preparation and Its Use, Derwent Abstract" SK 284392, Aug. 10, 1994, pp. 1-2.

*Primary Examiner* — Felicia C Turner
(74) *Attorney, Agent, or Firm* — Grüneberg and Myers PLLC

(57) ABSTRACT

The present invention relates to a novel liquid or crystalline methionine composition, obtained by means of biomass bioconversion by means of microorganisms that are suitable for producing methionine.

19 Claims, No Drawings

METHIONINE-RICH COMPOSITION FOR FEEDING ANIMALS

CROSS-REFERENCE TO RELATED APPLICATIONS

This application is a continuation of U.S. application Ser. No. 13/501,490, filed Apr. 12, 2012, which is the U.S. national stage application of International Patent Application No. PCT/EP2010/065428, filed Oct. 14, 2010, the disclosures of which are hereby incorporated by reference in their entireties, including all figures, tables and amino acid or nucleic acid sequences.

The present invention relates to a novel liquid or crystalline methionine composition, obtained by means of biomass bioconversion by means of microorganisms that are suitable for producing methionine.

Methionine, like other sulfur-containing amino acids, is essential to cell metabolism. However, methionine is not produced by animals, which therefore have to find it in sufficient amounts in their diet. It is therefore produced industrially to be added as food supplements, in particular feed supplements for feeding animals. Methionine can also be used as a medicament in the treatment or prevention of various diseases, such as allergies or rheumatoid fevers.

The usual sources of methionine are either proteins of animal origin, or chemical synthesis. However, the reduction in the use of animal proteins following the development of BSE or bird flu has led to an increase in the demand for synthetic methionine.

D,L-Methionine is generally produced from fossil resources and from petrochemical derivatives, in particular from acrolein, from methyl mercaptan and from cyanides. In order to obtain the more active L enantiomer, additional steps of racemic resolution are required, which drastically increase the production costs thereof.

Today, the production of methionine by bioconversion constitutes an advantageous alternative to petrochemistry owing to the increased scarcity of fossil resources and to the increase in the cost of raw materials. However, the implementation of these processes requires the availability of suitable microorganisms for producing methionine by biofermentation on a carbon source.

The first industrially efficient solutions have been published, and in particular described in patent applications WO 2005/111202, WO 2007/017710, WO 2007/077041 and WO 2009/043803. Other methionine-producing microorganisms are also described in patent applications WO 2004/038 013, WO 2006/001616, WO 2006/138689 and WO 2007/012078, in particular.

However, the large-scale production of biosynthetic methionine encounters problems specific to the recovery of chemical molecules in a fermenter, in particular for the purification of the final products. In this case, the quality of the crude mixture obtained, the content of impurities and the nature of said impurities are of great importance.

The present invention therefore relates to a novel liquid methionine composition, resulting from a fermentation process, the content of methionine and of other constituents of which allows easier purification, in particular for obtaining a solid product containing a higher methionine content relative to the dry residues of the liquid composition.

The methionine composition is the result of a fermentation process, i.e. a process of biomass conversion, in which a microorganism that has been modified to produce methionine is cultured on a suitable culture medium comprising a carbon source. The carbon sources are chosen from all the carbon sources that can be metabolized by a microorganism, and in particular glucose, sucrose, monosaccharides or oligosaccharides, starch and its derivatives, and mixtures thereof.

Consequently, the composition according to the invention differs from methionine compositions obtained by other processes, in particular chemical processes, by virtue of the content of carbon isotopes of the methionine molecules which are specific for fermentation products as opposed to products resulting from fossil raw materials. The composition according to the invention may also differ from the methionine compositions obtained by other processes by virtue of the nature and/or the content of the impurities present.

The composition according to the invention is a methionine composition resulting from a fermentation process, comprising from 50 to 95% by weight of methionine and comprising less than 10% by weight of isoleucine. Preferentially, the composition comprises from 60 to 95% by weight of methionine.

Unless otherwise indicated, the percentages are given herein by weight of the dry residues of the composition, whether it is a liquid or solid composition.

More particularly, the composition according to the invention is a feed additive comprising, or consisting of, a methionine composition resulting from a fermentation process, in particular as defined in the present description.

According to one of the aspects of the present invention, a subject thereof is a feed additive for feeding animals, comprising, or consisting of, a methionine composition resulting from a fermentation process, comprising:
  from 60 to 95%, especially from 70 to 95%, by weight of methionine,
  from 0.05 to 2.5%, especially from 0.1 to 2%, in particular from 0.3 to 2%, by weight of N-acetylmethionine, and
  from 0.05 to 3.5%, especially from 0.2 to 3%, in particular from 0.3 to 3%, by weight of isoleucine.

Quite particularly, the feed additive may comprise, or consist of, a composition comprising, in addition:
  from 1.0 to 6.0% by weight, especially from 2.0 to 5.0% by weight, of amino acids other than methionine, N-acetylmethionine and isoleucine,
  from 0.1 to 2% by weight, especially from 0.2 to 1.5% by weight, of total sugars, and
  from 0.05 to 2.5% by weight, especially from 0.1 to 2% by weight, in particular from 0.2 to 1.5% by weight, of lipids.

The composition or the additive according to the invention may be an aqueous liquid composition, and in this case, it is more particularly the composition obtained at the end of fermentation, after removal of the biomass and of part of the organic impurities. It will be denoted a "crude" composition.

According to one variant, when the composition, or the additive, is liquid, it is in the form of a solution, in particular a clear solution. This composition, or additive, in liquid form may be free of methionine in solid form and in particular crystalline form.

The composition, or the additive, in liquid form may, moreover, be in the form of a dispersion.

Quite particularly, the methionine content of this composition or additive in liquid form is less than or equal to 8 g/100 ml, especially less than or equal to 4.8 g/100 ml, in particular less than or equal to 4.5 g/100 ml, or even less than or equal to 4 g/100 ml of liquid composition.

Advantageously, the liquid composition or liquid additive according to the invention comprises between 60 and 85% by weight of methionine, more particularly between 70 and 85%.

The liquid composition or liquid additive may comprise a methionine content ranging from 60 to 80% by weight, especially from 65 to 75% by weight.

The liquid composition or liquid additive may comprise an N-acetylmethionine content ranging from 0.5 to 2.0% by weight, especially from 0.75 to 1.75% by weight.

The liquid composition or liquid additive may comprise an isoleucine content ranging from 0.20 to 1.5% by weight, especially from 0.3 to 1.0% by weight.

The liquid composition or liquid additive may comprise a content of amino acids other than methionine, N-acetylmethionine and isoleucine ranging from 2 to 6% by weight, especially from 3 to 5% by weight.

The liquid composition or liquid additive may comprise a total sugar content ranging from 0.5 to 2% by weight, especially from 0.75 to 1.5% by weight.

The liquid composition or liquid additive may comprise a lipid content ranging from 0.05 to 2.5% by weight, especially from 0.075 to 1.5% by weight.

Thus, according to a first embodiment, the feed additive in liquid form comprises, or consists of, a composition comprising:
  from 60 to 80% by weight, especially from 65 to 75% by weight, of methionine,
  from 0.5 to 2.0% by weight, especially from 0.75 to 1.75% by weight, of N-acetylmethionine, and
  from 0.20 to 1.5% by weight, especially from 0.3 to 1.0% by weight, of isoleucine.

Even more particularly, the feed additive in liquid form comprises, or consists of, a composition comprising:
  from 2 to 6% by weight, especially from 3 to 5% by weight, of amino acids other than methionine, N-acetylmethionine and isoleucine,
  from 0.5 to 2% by weight, especially from 0.75 to 1.5% by weight, of total sugars, and
  from 0.05 to 2.5% by weight, especially from 0.075 to 1.5% by weight, of lipids.

The liquid composition or liquid additive may also comprise a methionine content ranging from 70 to 90% by weight, especially from 75 to 85% by weight.

The liquid composition or liquid additive may comprise an N-acetylmethionine content ranging from 0.05 to 2.5% by weight, especially from 0.075 to 2.0% by weight.

The liquid composition or liquid additive may comprise an isoleucine content ranging from 0.1 to 1.0% by weight, especially from 0.3 to 0.75% by weight.

The liquid composition or liquid additive may comprise a content of amino acids other than methionine, N-acetylmethionine and isoleucine ranging from 2 to 6% by weight, especially from 3 to 5% by weight.

The liquid composition or liquid additive may comprise a total sugar content ranging from 0.25 to 2% by weight, especially from 0.5 to 1.5% by weight.

The liquid composition or liquid additive may comprise a lipid content ranging from 0.05 to 2.5% by weight, especially from 0.075 to 2.0% by weight.

Thus, according to a second embodiment, the feed additive in liquid form comprises, or consists of, a composition comprising:
  from 70 to 90% by weight, especially from 75 to 85% by weight, of methionine,
  from 0.05 to 2.5% by weight, especially from 0.075 to 2.0% by weight, of N-acetylmethionine, and
  from 0.1 to 1.0% by weight, especially from 0.3 to 0.75% by weight, of isoleucine.

Even more particularly, the feed additive in liquid form comprises, or consists of, a composition comprising:
  from 2 to 6% by weight, especially from 3 to 5% by weight, of amino acids other than methionine, N-acetylmethionine and isoleucine,
  from 0.25 to 2% by weight, especially from 0.5 to 1.5% by weight, of total sugars, and
  from 0.05 to 2.5% by weight, especially from 0.05 to 2.0% by weight, of lipids.

The composition according to the invention may be in solid form. This composition is more particularly the product of crystallization of the methionine contained in the liquid composition previously defined, after a purification treatment.

Advantageously, the solid composition according to the invention comprises between 75 and 95% by weight of methionine, more particularly between 85 and 95%.

Moreover, the feed additive may be in solid form.

The solid composition or solid additive may comprise a methionine content ranging from 80 to 95% by weight, especially from 85 to 95% by weight.

The solid composition or solid additive may comprise an N-acetylmethionine content ranging from 0.05 to 0.5% by weight, especially from 0.05 to 0.3% by weight.

The solid composition or solid additive may comprise an isoleucine content ranging from 0.05 to 5.0% by weight, especially from 0.1 to 3.0% by weight.

The solid composition or solid additive may comprise a content of amino acids other than methionine, N-acetylmethionine and isoleucine ranging from 1.0 to 5.0% by weight, especially from 1.5 to 4.0% by weight.

The solid composition or solid additive may comprise a total sugar content ranging from 0.1 to 1.5% by weight, especially from 0.2 to 1.0% by weight.

The solid composition or solid additive may comprise a lipid content of less than or equal to 0.3% by weight.

According to a third embodiment, the feed additive, especially solid feed additive, comprises, or consists of, a composition comprising:
  from 80 to 95% by weight, especially from 85 to 95% by weight, of methionine,
  from 0.05 to 0.5% by weight, especially from 0.05 to 0.3% by weight, of N-acetylmethionine, and
  from 0.1 to 5.0% by weight, especially from 0.1 to 3.0% by weight, of isoleucine.

Even more particularly, the feed additive in liquid form comprises, or consists of, a composition comprising:
  from 1.0 to 5.0% by weight, especially from 1.5 to 4.0% by weight, of amino acids other than methionine, N-acetylmethionine and isoleucine,
  from 0.1 to 1.5% by weight, especially from 0.2 to 1.0% by weight, of total sugars, and
  less than 0.3% by weight of lipids.

The composition according to the invention, resulting from a fermentation process, advantageously comprises less than 10% by weight of isoleucine, more particularly less than 5% by weight.

The composition according to the invention is a composition which generally comprises other residues resulting from the methionine bioproduction process, and in particular other amino acids. The content of amino acids other than methionine and isoleucine is advantageously less than 10% by weight. Many amino acids are present as residues in the composition according to the invention, and the content of each amino acid other than methionine and isoleucine, taken individually, is advantageously less than 2% by weight, more advantageously less than 1% by weight.

The composition according to the invention advantageously comprises less than 0.2% of ash, and in particular from 0.01 to 0.2% of ash.

The N-acetylmethionine content is advantageously between 0 and 2% by weight. It will especially depend on the liquid or solid nature of the crude composition. Its content is close to 0 in the solid composition.

The composition according to the invention also and advantageously comprises less than 2% by weight of lipids and less than 2% by weight of sugars, advantageously less than 1% by weight.

The process for obtaining the compositions consists of several steps:

A) clarifying the fermentation medium and removing the insoluble and soluble organic impurities from said fermentation medium in order to obtain a liquid crude composition, where appropriate, B) demineralizing the liquid crude solution in order to remove the cations and anions from said fermentation medium, in order to obtain a demineralized liquid crude composition, and to guarantee obtaining a solid methionine with a hygroscopic profile close to that of chemical methionine, where appropriate, C) crystallizing the crude methionine from the demineralized liquid solution, and D) separating, optionally washing, and drying and optionally milling the methionine crystals in order to obtain a solid crude composition.

It is understood that a composition comprising methionine crystallized from a solution of methionine is also part of the invention.

For the purpose of the invention, the term "insoluble organic impurities" is intended to mean the residual insoluble particles, proteins and biomass.

The term "soluble organic impurities" is intended to mean all the soluble particles contaminating the fermentation medium, especially the macromolecules of the soluble protein type and polysaccharides.

The first step of the process consists in clarifying the fermentation medium and in removing the organic impurities. The clarification of the medium is carried out by any method known as such by those skilled in the art, which method is chosen, for example, from the group consisting of flocculation, decanting, membrane techniques (microfiltration, ultrafiltration, nanofiltration and reverse osmosis) and centrifugation. The removal of the soluble organic impurities is carried out by any method known as such by those skilled in the art, which method is chosen, for example, from the group consisting of ultrafiltration, heat treatment, treatment with an adsorbent of activated carbon type, and enzymatic hydrolysis. The removal of these soluble impurities makes it possible to ensure that the cooked mass behaves correctly during crystallization. Indeed, without this step, the cooked mass has a pasty homogeneous appearance, producing very fine crystals and penalizing the separation and washing of said crystals. Consequently, the purity of the crystals is reduced.

The second step consists in removing the mineral salts from the resulting solution. This step can be carried out by conventional electrodialysis (Eurodia®) and/or by treatment on a cation exchange resin in H+ form (Purolite® C120, Purolite® C150, Purolite® C160, etc.) and/or anion exchange resin (Lewatit® 54228, Lewatit® 54528, Rohm & Haas FPA91, etc.). Treatment with ion exchange resins will be preferred to conventional electrodialysis for reasons of cost and salt reduction efficiency. This step makes it possible, inter alia, to reduce the salt content in the solid methionine and thus to ensure minimum water uptake for good stability during storage.

The third step consists in crystallizing the methionine so as to recover the crude methionine in solid form. This crystallization step can be carried out by means of technology chosen from the group consisting of crystallization by cooling, crystallization by evaporation-crystallization and adiabatic crystallization. The applicant company recommends using evaporation-crystallization. If evaporation-crystallization is selected, the applicant company recommends pre-concentrating the crude methionine solution by vacuum evaporation using a falling-film evaporator in order to approach supersaturation. The pre-concentrated solution is therefore transferred into a crystallizer of Draft tube type, for example, so as to be further concentrated and crystallized therein. The methionine solubility at 35° C. is approximately 70 g/l. If the solution is concentrated to approximately 250 g/l, under a vacuum ensuring a temperature of 35° C., the methionine recovery yield is >70%. Under these conditions, and by virtue of the removal of the soluble impurities, the solid methionine crystallizes in the form of spongy spheres which are easy to separate from the mother liquors.

The fourth step consists in separating the resulting solid crude methionine, in washing it and in drying it. The solid crude methionine is recovered by any method known as such by those skilled in the art, which method is chosen, for example, from the group consisting of centrifugation, suction filtration and frontal filtration (on a drum, on a filter press, etc.). In the latter case, the crude methionine is therefore retained on a 40 μm cloth and the mother liquors pass through. The crude methionine cake is then washed with 1 to 10 BV of water, preferably demineralized water. The solid crude methionine is then dried and optionally milled in order to classify the particles.

The liquid and solid crude composition obtained is described in table 1 below:

TABLE 1

| G/100 g of dry residue | Liquid crude composition | Solid crude composition |
| --- | --- | --- |
| L-Methionine (L-MET) | 50-85 | 75-95 |
| N-Acetylmethionine (NAM) | <2 | <1 |
| Isoleucine (ISO) | <10 | <10 |
| Unknown AA derivatives | <2 | <2 |
| Valine | <2 | <2 |
| Phenylalanine | <2 | <2 |
| Leucine | <2 | <2 |
| Aspartic acid | <2 | <2 |
| Threonine | <2 | <2 |
| Alanine | <2 | <2 |
| Lysine | <2 | <2 |
| Arginine | <2 | <2 |
| Cystine | <2 | <2 |
| Glutamine | <2 | <2 |
| Tyrosine | <2 | <2 |
| Glutamic acid | <2 | <2 |
| Glycine | <2 | <2 |
| Citrulline | <2 | <2 |
| Total AAs other than L-MET, NAM and ISO | <10 | <10 |
| Total sugars | <5 | <2 |
| Lipids | <2 | <2 |
| Organic acids | <3 | <2 |
| Thiosulfates | <7 | <1 |
| Sulfates | <1.5 | <2 |
| Phosphates | <0.2 | <1 |
| Chlorides | <0.2 | <0.5 |

TABLE 1-continued

| G/100 g of dry residue | Liquid crude composition | Solid crude composition |
|---|---|---|
| Ammonium | <3 | <1.5 |
| Sodium | <1 | <0.01 |
| Potassium | <1 | <0.05 |
| Magnesium | <0.2 | <0.01 |
| Calcium | <0.1 | <0.01 |
| Others | <10 | <5 |

The "unknown AA derivatives" line corresponds to entities which are similar to AAs and in the process of being identified.

The "others" line corresponds to entities not identified at this time.

The crude composition according to the invention can advantageously be used directly, in solid or liquid form, in the feeding of animals, as a feed supplement or additive given to the animals, mixed with the bolus given to each animal, in a premix, or in the form of a premixed or extemporaneously mixed composition, or independently of the other feeds.

The invention therefore also relates to a feed additive comprising the methionine composition according to the invention.

According to yet another of the aspects of the invention, a subject thereof is also a process for preparing a feed additive for feeding animals, especially as defined above, comprising, or consisting of, at least the following step which, using a fermentation medium from a methionine preparation process in which a microorganism that has been modified to produce methionine is cultured on a suitable culture medium comprising a carbon source, consists in:

A) clarifying the fermentation medium and removing the insoluble and soluble organic impurities from said fermentation medium in order to obtain a liquid crude composition comprising:
   from 60 to 80% by weight, especially from 65 to 75% by weight, of methionine,
   from 0.5 to 2.0% by weight, especially from 0.75 to 1.75% by weight, of N-acetylmethionine, and
   from 0.20 to 1.5% by weight, especially from 0.3 to 1.0% by weight, of isoleucine, and
E) recovering the feed additive.

The preparation process can result in a liquid crude composition comprising, in addition:
   from 2 to 6% by weight, especially from 3 to 5% by weight, of amino acids other than methionine, N-acetylmethionine and isoleucine,
   from 0.5 to 2% by weight, especially from 0.75 to 1.5% by weight, of total sugars, and
   from 0.05 to 2.5% by weight, especially from 0.075 to 1.5% by weight, of lipids.

The process for preparing a feed additive may comprise, in addition, a step which consists in:
B) demineralizing the liquid crude solution in order to remove the cations and anions from said fermentation medium, especially in order to obtain a demineralized liquid crude composition comprising:
   from 70 to 90% by weight, especially from 75 to 85% by weight, of methionine,
   from 0.05 to 2.5% by weight, especially from 0.075 to 2.0% by weight, of N-acetylmethionine, and
   from 0.1 to 1.0% by weight, especially from 0.3 to 0.75% by weight, of isoleucine.

The process for preparing a feed additive can make it possible to obtain a demineralized liquid crude composition comprising, in addition:
   from 2 to 6% by weight, especially from 3 to 5% by weight, of amino acids other than methionine, N-acetylmethionine and isoleucine,
   from 0.25 to 2% by weight, especially from 0.5 to 1.5% by weight, of total sugars, and
   from 0.05 to 2.5% by weight, especially from 0.075 to 2.0% by weight, of lipids.

More particularly, the process for preparing a feed additive makes it possible to obtain a liquid feed additive, and especially said process does not comprise a crystallization step.

The process for preparing a feed additive may comprise, in addition, the step which consists in:
C) crystallizing solid crude methionine from the optionally demineralized, liquid crude composition.

The process for preparing a feed additive may further comprise the step which consists in:
D) separating, optionally washing, and optionally milling methionine crystals in order to obtain a solid crude composition.

Finally, the process for preparing a feed additive can make it possible to obtain a solid crude composition comprising:
   from 80 to 95% by weight, especially from 85 to 95% by weight, of methionine,
   from 0.05 to 0.5% by weight, especially from 0.05 to 0.3% by weight, of N-acetylmethionine, and
   from 0.05 to 5.0% by weight, especially from 0.1 to 3.0% by weight, of isoleucine.

The process for preparing a feed additive can make it possible for the solid crude methionine composition or the solid crude composition to comprise, in addition:
   from 1.0 to 5.0% by weight, especially from 1.5 to 4.0% by weight, of amino acids other than methionine, N-acetylmethionine and isoleucine,
   from 0.1 to 1.5% by weight, especially from 0.2 to 1.0% by weight, of total sugars, and
   less than 0.3% by weight of lipids.

Moreover, a subject of the invention is also a process for preparing a feed supplemented with methionine, comprising at least one step of adding a feed composition or feed additive according to the invention.

According to one variant, this addition is carried out by adding a composition or an additive in liquid form to a solid feed. This can in particular be carried out extemporaneously. The addition can thus be carried out by simple spraying of the composition or of the additive.

According to another variant, this addition is carried out by adding a composition or an additive in liquid form to a liquid feed, such as drinking water. This can also be carried out extemporaneously.

According to yet another of the aspects of the invention, a subject thereof is the use of a composition as defined above, for preparing a feed additive and/or a feed supplemented with methionine.

Those skilled in the art are well aware of the amounts of methionine necessary for feeding animals in a diet suitable for each animal and will be able to determine how to use the composition according to the invention and in what amount. In particular, the liquid crude form is particularly suitable for its provision of trace elements and water in order to facilitate the metering-out, mixing and hydrating of the usual feeds of the animal.

The crude methionine composition according to the invention may be the result of any methionine bioproduction process with the culturing of a microorganism optimized to promote methionine synthesis, whether it is a bacterium, yeasts or fungi (molds). Advantageously, the microorganism is chosen from *Enterobacteriaceae*, *Bacillaceae*, *Streptomycetaceae* and *Corynebacteriaceae*. More particularly, the microorganism is a species chosen from the *Escherichia*, *Klebsiella*, *Pantoea*, *Salmonella* or *Corynebacterium* species. More particularly, the microorganism is chosen from the *Escherichia coli* or *Corynebacterium glutamicum* species.

In one particular embodiment of the invention, the crude methionine composition according to the invention comes from the culturing of the microorganisms described in international application WO 2009/043803, the content of which is incorporated herein by way of reference, and more particularly the microorganisms described in the exemplary embodiments.

The invention is more particularly illustrated in the exemplary embodiment set out hereinafter.

A methionine-producing *E. coli* strain of genotype MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA ΔpurU (pME101-thrA*1-cysE-PgapA-metA*11) (pCC1BAC-serB-serA-serC), described in international application WO 2009/043803, is grown under fermentation culture conditions according to the method described in this same international application.

EXAMPLE 1: PREPARATION OF CRUDE METHIONINE

A fermentation must resulting from the processing of the strain previously described and containing L-methionine is purified as follows.

A) Removal of the Insoluble Organic Impurities: The Biomass

The removal is carried out by tangential filtration on a membrane having a pore diameter of 100 nm, at between 40 and 80° C. (membrane of ceramic type with a channel diameter of 3.5 mm).

The temperature is preferentially maintained at 40° C. with a transmembrane pressure of 1 bar and diafiltration with 20% of demineralized water.

Under these conditions, the average flow rate is 30 L/h/m$^2$ and the permeate obtained is clear and bright. The permeate, freed of the biomass and of the insoluble particles, still contains soluble organic impurities, in particular soluble sugars and proteins that it is advisable to remove before crystallization.

B) Removal of the Soluble Organic Impurities: The Soluble Sugars and Macromolecules The objective of this step is to remove the sugars (polysaccharides) and the macromolecules contained in the fermentation must. This is because these impurities negatively affect the behavior of the cooked mass (homogeneous, bound appearance, very fine crystals) and the recovery of the solid phase during the L-methionine crystallization step.

This removal can be carried out by ultrafiltration on a ceramic membrane which has a cut-off threshold of 5 kDa. At 40° C., the filtration flow rate is on average 25 L/h/m$^2$, and approximately 70% of the macromolecules are retained in the retentate.

The permeate, corresponding to the liquid crude composition, has the following composition:

TABLE 2

| g/100 g of dry residue | Liquid crude composition |
|---|---|
| L-Methionine (L-MET) | 72.6 |
| N-Acetylmethionine (NAM) | 1.36 |
| Isoleucine (ISO) | 0.50 |
| Unknown AA derivative | 1.2 |
| Valine | 0.61 |
| Phenylalanine | 0.58 |
| Leucine | 0.18 |
| Aspartic acid | 0.25 |
| Threonine | 0.26 |
| Alanine | 0.39 |
| Lysine | 0.10 |
| Arginine | 0.04 |
| Cystine | 0.02 |
| Glutamine | 0.17 |
| Tyrosine | 0.28 |
| Glutamic acid | 0.17 |
| Glycine | 0.10 |
| Citrulline | 0.15 |
| AAs other than MET, NAM and ISO | 3.99 |
| Total sugars | 0.89 |
| Lipids | 1.05 |
| Organic acids | <3 |
| Thiosulfates | 4.72 |
| Sulfates | 1.04 |
| Phosphates | 0.09 |
| Chlorides | 0.10 |
| Ammonium | 2.26 |
| Sodium | 0.58 |
| Potassium | 0.42 |
| Magnesium | 0.10 |
| Calcium | 0.02 |
| Others | 8.47 |

This permeate is then demineralized before being crystallized so as to give the solid crude composition.

C) Permeate Demineralization:

The objective of this demineralization step is to remove the inorganic anions and cations present in the fermentation must containing the L-methionine.

It can be carried out by conventional electrodialysis and/or treatment on a strong cation exchange resin and on an anion exchange resin.

When the treatment is carried out on ion exchange resins, the percentage demineralization is greater than that achieved by conventional electrodialysis. Thus, with a strong cation exchange resin (type Purolite® C120, C150), it is possible to remove more than 85% of the cations while at the same time guaranteeing a methionine yield >95% by correct proportioning of the resin volume. Indeed, since methionine is amphoteric, it will also bind to the resin, but the affinity of the cations to the resin is greater than that of the methionine: the methionine is therefore displaced by the cations.

By the same affinity mechanism, the permeate treated on an anion exchange resin (type Rohm & Haas, FPA91, Bayer 4228, etc.) undergoes a decrease of more than 95% in its anion content, with a methionine yield >80%.

After demineralization treatment, the solution has the following composition:

TABLE 3

| Compounds | Content (%/dry) |
|---|---|
| L-Methionine (MET) | 79.38 |
| N-Acetylmethionine (NAM) | 1.49 |
| Isoleucine (ISO) | 0.54 |
| AAs other than MET, NAM and ISO | 4.36 |
| Total sugars | 0.77 |

TABLE 3-continued

| Compounds | Content (%/dry) |
|---|---|
| Lipids | 1.18 |
| Succinic acid | 1.10 |
| Citric acid | 0.16 |
| Thiosulfate | 0.23 |
| Sulfate | 0.12 |
| Phosphate | 0.05 |
| Chloride | 0.10 |
| $NH_4$ | 0.25 |
| Na | 0.08 |
| K | 0.11 |
| Mg | 0.10 |
| Ca | 0.02 |
| Fe | 0.01 |
| Others | 9.55 |

This solution is then concentrated in order to crystallize the L-methionine.

D) Crystallization

The demineralized solution is pre-concentrated by evaporation of the water at 50° C. on a Wiegand® falling-film vacuum evaporator. The concentration factor is about from 2 to 5 depending on the initial concentration of L-methionine.

It is in this case equal to 3 so as to approach supersaturation at 50° C. (80 g/L).

The pre-concentrated solution is then transferred into a forced-circulation evapocrystallizer and is further concentrated and crystallized therein under vacuum (50 mbar) at approximately 35° C. The concentration factor applied in this evapocrystallizer is approximately 3, so as to achieve 240 g/L.

After separation on a Choquenet® filter press and washing with one volume of demineralized water per volume of cake, the crystals are dried on a fluidized bed at 45° C. (of the Aeromatic® type).

Under these conditions, the L-methionine recovery yield is >80% for a purity >85%/dry.

The composition of the solid crude L-methionine is given in the following table:

TABLE 4

| g/100 g of dry residue | Solid crude composition |
|---|---|
| L-Methionine (L-MET) | 89.49 |
| N-Acetylmethionine (NAM) | 0.13 |
| Isoleucine (ISO) | 2.41 |
| Unknown AA derivative | 0.50 |
| Valine | 0.69 |
| Phenylalanine | 0.44 |
| Leucine | 0.20 |
| Aspartic acid | 0.09 |
| Threonine | 0.19 |
| Alanine | 0.15 |
| Lysine | 0.05 |
| Arginine | 0.04 |
| Cystine | 0.02 |
| Glutamine | 0.13 |
| Tyrosine | 0.44 |
| Glutamic acid | 0.19 |
| Glycine | 0.18 |
| Citrulline | 0.61 |
| Total AAs other than L-MET, NAM and ISO | 2.37 |
| Total sugars | 0.31 |
| Lipids | <1 |
| Organic acids | <1 |
| Thiosulfates | 0.02 |
| Sulfates | 0.02 |
| Phosphates | 0.05 |
| Chlorides | 0.01 |
| Ammonium | 0.04 |
| Sodium | 0.01 |
| Potassium | 0.03 |
| Magnesium | <0.01 |
| Calcium | <0.01 |
| Others | 3.95 |

The mother liquor still contains close to 40%/sec of methionine. In order to optimize the overall yield, it is possible to totally or partially recycle the mother liquor upstream of the process, in liquid form or after a second crystallization crop, before or after an appropriate treatment.

The solid crude methionine obtained from the process described in the example according to the invention has a hygroscopic stability comparable to that of chemical methionine.

EXAMPLE 2: FEEDING OF ANIMALS

The crude methionine previously obtained in solid form is added to a basic feed for broiler chickens.

The basic feed has the following composition:

TABLE 5

| | % |
|---|---|
| Wheat | 61.93 |
| Cooked soya seed | 16.20 |
| Palm oil | 0.50 |
| Soya oilcakes | 18.40 |
| Dicalcium phosphate | 0.94 |
| Meal carbonate | 0.86 |
| Salt | 0.24 |
| Sodium bicarbonate | 0.20 |
| Liquid lysine 50% | 0.20 |
| Choline chloride 75% | 0.06 |
| Prem. threonine 25 | 0.03 |
| Prem. phytase | 0.04 |
| Poultry premix | 0.40 |

This feed is supplemented with crude methionine so as to obtain compositions comprising various crude methionine contents, at 0.05%, 0.1%, 0.15%, 0.2% and 0.25% of added methionine (corresponding to, respectively, approximately 0.063%, 0.125%, 0.188%, 0.250% and 0.313% of solid crude methionine added to the feed).

The animals are divided up into groups and fed with the basic feed as control, or with a feed supplemented with crude methionine according to the invention, and then weighed at 1 day, 14 days and 28 days.

A clear improvement in performance levels is noted for the feeds supplemented with the methionine according to the invention. Optimum efficiency is identified at around 0.4% of methionine in the final feed, i.e. from 0.1 to 0.15% of added methionine (the basic feed has a methionine content of about 0.29%).

When the same experiment is carried out with DL-methionine of chemical origin, an optimum is observed at around approximately 0.48% of methionine in the final feed, i.e. approximately 0.19% of added methionine.

The crude methionine according to the invention therefore appears to be used better by the animal than the DL-methionine of chemical origin.

The invention claimed is:

1. A feed additive for feeding animals comprising a methionine composition resulting from a fermentation process, said methionine composition comprising:
   from 60 to 95% by weight of methionine;
   from 0.05 to 2.5% by weight of N-acetylmethionine; and
   from 0.05 to 3.5% by weight of isoleucine.

2. The feed additive of claim 1, said methionine composition further comprising:
   from 1.0 to 6.0% by weight of amino acids other than methionine, N-acetylmethionine and isoleucine;
   from 0.1 to 2% by weight of total sugars; and
   from 0.05 to 2.5% by weight of lipids.

3. The feed additive of claim 1, wherein said additive is a liquid.

4. The feed additive of claim 1, wherein said methionine composition comprises:
   from 60 to 80% by weight of methionine;
   from 0.5 to 2.0% by weight of N-acetylmethionine; and
   from 0.20 to 1.5% by weight isoleucine.

5. The feed additive of claim 2, said methionine composition further comprising:
   from 2 to 6% by weight of amino acids other than methionine, N-acetylmethionine and isoleucine;
   from 0.5 to 2% by weight of total sugars; and
   from 0.05 to 2.5% by weight of lipids.

6. The feed additive of claim 1, said methionine composition comprising:
   from 70 to 90% by weight of methionine;
   from 0.05 to 2.5% by weight of N-acetylmethionine; and
   from 0.10 to 1.0% by weight of isoleucine.

7. The feed additive of claim 2, said methionine composition further comprising:
   from 2 to 6% by weight of amino acids other than methionine, N-acetylmethionine and isoleucine;
   from 0.25 to 2% by weight of total sugars; and
   from 0.05 to 2.5% by weight of lipids.

8. The feed additive of claim 2, wherein said additive is a liquid.

9. The feed additive of claim 1, said methionine composition comprising:
   from 80 to 95% by weight of methionine;
   from 0.05 to 0.5% by weight of N-acetylmethionine; and
   from 0.05 to 5.0% by weight of isoleucine.

10. The feed additive of claim 2, said methionine composition further comprising:
    from 1.0 to 5.0% by weight of amino acids other than methionine, N-acetylmethionine and isoleucine;
    from 0.1 to 1.5% by weight of total sugars, and less than 0.3% by weight of lipids.

11. A process for preparing the feed additive of claim 1 comprising:
    clarifying fermentation medium in which a microorganism that has been modified to produce methionine has been cultured and removing insoluble and soluble organic impurities from said fermentation medium to obtain a liquid crude composition; and
    recovering the feed additive.

12. The process for preparing a feed additive of claim 11, wherein the liquid crude composition further comprises:
    from 2 to 6% by weight of amino acids other than methionine, N-acetylmethionine and isoleucine;
    from 0.1 to 2% by weight of total sugars; and
    from 0.05 to 2.5% by weight of lipids.

13. The process for preparing a feed additive of claim 11, said process further comprising:
    demineralizing the liquid crude solution in order to remove cations and anions from said fermentation medium to obtain a demineralized liquid crude composition comprising:
    from 70 to 90% by weight of methionine;
    from 0.05 to 2.5% by weight of N-acetylmethionine; and
    from 0.10 to 1.0% by weight of isoleucine.

14. The process for preparing a feed additive of claim 13, said demineralized liquid crude composition further comprising:
    from 2 to 6% by weight of amino acids other than methionine, N-acetylmethionine and isoleucine;
    from 0.25 to 2% by weight of total sugars; and
    from 0.05 to 2.5% by weight of lipids.

15. The process for preparing a feed additive of claim 11, wherein the feed additive is liquid and said process does not comprise a crystallization step.

16. The process for preparing a feed additive of claim 11, further comprising:
    crystallizing solid crude methionine from an optionally demineralized, liquid crude composition.

17. The process for preparing a feed additive of claim 16, said method further comprising:
    separating, optionally washing, and optionally milling methionine crystals in order to obtain a solid crude composition.

18. The process for preparing a feed additive of claim 16, wherein said solid crude composition comprises:
    from 80 to 95% by weight of methionine;
    from 0.05 to 0.5% by weight of N-acetylmethionine; and
    from 0.05 to 5.0% by weight of isoleucine.

19. The process for preparing a feed additive of claim 18, wherein the solid crude methionine composition further comprises:
    from 1.0 to 5.0% by weight of amino acids other than methionine, N-acetylmethionine and isoleucine;
    from 0.1 to 1.5% by weight of total sugars; and
    less than 0.3% by weight of lipids.

* * * * *